(12) United States Patent
Chen et al.

(10) Patent No.: US 11,163,086 B2
(45) Date of Patent: Nov. 2, 2021

(54) APPARATUS AND METHOD FOR WELLBORE IMAGING IN OIL-BASED MUD

(71) Applicant: University of Houston System, Houston, TX (US)

(72) Inventors: Jiefu Chen, Cypress, TX (US); Xinyu Liu, Houston, TX (US); David R. Jackson, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 103 days.

(21) Appl. No.: 16/477,109

(22) PCT Filed: Jan. 10, 2018

(86) PCT No.: PCT/US2018/013049
§ 371 (c)(1),
(2) Date: Jul. 10, 2019

(87) PCT Pub. No.: WO2018/132397
PCT Pub. Date: Jul. 19, 2018

(65) Prior Publication Data
US 2019/0353820 A1 Nov. 21, 2019

Related U.S. Application Data

(60) Provisional application No. 62/444,674, filed on Jan. 10, 2017.

(51) Int. Cl.
*G01V 3/30* (2006.01)
*E21B 47/002* (2012.01)
(Continued)

(52) U.S. Cl.
CPC .............. *G01V 3/30* (2013.01); *E21B 47/002* (2020.05); *E21B 49/00* (2013.01); *G01N 22/00* (2013.01)

(58) Field of Classification Search
CPC ....... G01V 3/30; G01N 22/00; G01N 22/2823
See application file for complete search history.

(56) References Cited

U.S. PATENT DOCUMENTS 5,280,243 A   1/1994 Miller
5,406,214 A * 4/1995 Boda ...................... G01N 22/00
                                                          324/642
(Continued)

FOREIGN PATENT DOCUMENTS

JP    8-288707 A    11/1996
WO    2016203712 A1 12/2016

OTHER PUBLICATIONS

International Search Report and Written Opinion dated May 1, 2018 for corresponding International Application No. PCT/US2018/013049.

*Primary Examiner* — Dominic E Hawkins
(74) *Attorney, Agent, or Firm* — Winstead PC

(57) ABSTRACT

An oil-based mud wellbore imaging apparatus for measuring formation permittivity and resistivity includes a reflectometry-type microwave scanning system. The system contains at least one high-Q microstrip resonator with one or more slots on the top surface. The microstrip resonator is excited by one port, which is fed with electromagnetic signals by a coaxial cable. From the phase detection of signal at the port, the formation resistivity and permittivity can be determined and corresponding borehole images can be generated.

15 Claims, 5 Drawing Sheets

(51) Int. Cl.
　　　*E21B 49/00*　　　(2006.01)
　　　*G01N 22/00*　　　(2006.01)

(56) References Cited

U.S. PATENT DOCUMENTS

| | | | |
|---|---|---|---|
| 6,191,588 B1 | 2/2001 | Chen | |
| 6,600,321 B2 | 7/2003 | Evans | |
| 6,809,521 B2 | 10/2004 | Tabarovsky et al. | |
| 7,299,131 B2 | 11/2007 | Tabarovsky et al. | |
| 7,696,756 B2 | 4/2010 | Morys et al. | |
| 7,888,941 B2 | 2/2011 | San Martin et al. | |
| 2005/0122115 A1* | 6/2005 | Maguire | G01R 33/345 324/322 |
| 2007/0235184 A1 | 10/2007 | Thompson et al. | |
| 2009/0213690 A1* | 8/2009 | Steinsiek | G01V 1/52 367/35 |
| 2011/0050225 A1* | 3/2011 | Prisner | G01R 33/282 324/307 |
| 2011/0291836 A1* | 12/2011 | Deavours | G06K 19/07775 340/572.7 |
| 2012/0223869 A1* | 9/2012 | Kim | H01Q 5/314 343/769 |
| 2013/0249756 A1* | 9/2013 | Honda | H01Q 21/0062 343/770 |
| 2014/0262321 A1 | 9/2014 | Fripp et al. | |
| 2015/0012216 A1 | 1/2015 | Liu et al. | |
| 2016/0025787 A1* | 1/2016 | Muller | G01N 22/00 324/612 |
| 2016/0141754 A1* | 5/2016 | Leyh | H01Q 13/00 342/372 |
| 2017/0237178 A1* | 8/2017 | Hu | H01Q 21/0025 343/700 MS |

* cited by examiner

APPARATUS AND METHOD FOR WELLBORE IMAGING IN OIL-BASED MUD

RELATED APPLICATIONS

This application is the National Stage of International Application No. PCT/US2018/013049, filed Jan. 10, 2018; which claims priority to U.S. Provisional Patent Application No. 62/444,674 filed on Jan. 10, 2017 which are specifically incorporated by reference in their entirety herein.

FIELD

The disclosure relates generally to downhole tools. The disclosure relates specifically to a borehole logging tool operable over a range of borehole sizes.

BACKGROUND

Well boreholes are typically drilled in earth formations to produce fluids from one or more of the penetrated formations. The fluids include water and hydrocarbons such as oil and gas. Measures of one or more borehole parameters such as wellbore relative dip angle, densities of fractures and vugs on the borehole wall, lamination of formation layers, etc., are useful over the life of the borehole, extending from the time that the borehole is drilled until the time of abandonment. It is therefore economically and operationally desirable to operate equipment for measuring various borehole parameters using a variety of borehole survey or "logging" systems. Such logging systems can include borehole images which provide information that is crucial for giving insights into the conditions of the borehole, secondary porosity, sequence stratigraphy, stress, etc. Such images reveal the fine-scale structure of the penetrated formations. The fine-scale structure includes stratifications such as shale/sand sequences, fractures, and non-homogeneities caused by irregular cementation and variations in pore size. Orientations of fractures and strata can also be identified, enabling more accurate reservoir flow modeling.

Two technology types are available for borehole imaging: acoustic and microresistivity. Acoustic imaging provides 360-degree borehole coverage. However, acoustic reflectivity limits the dynamic range so images are less detailed than with microresistivity. Microresistivity technology has been developed for decades and can generate very detailed images in electrically conductive mud. In an oil-based mud (OBM) scenario, there is a thin nonconductive film acting like an opaque curtain, resulting in the conventional microresistivity tools failing to generate informative images. The increasing use of oil and synthetic-based mud systems to limit drilling risks and improve efficiency poses many challenges for formation imaging since oil is non-conductive.

One commonly used OBM imaging tool consists of a sensor array having current and voltage electrodes. Current is injected into the formation layer. The potential difference between the electrodes sensor will be measured and resistivity can be calculated based on Ohm's Law. Because the oil-based mud usually has a high resistivity, a higher operating frequency needs to be picked to make sure the current from the transmitter electrodes can penetrate the layer of mud between the tool and the borehole wall. These tools have problems when used in non-conductive oil-based mud. In this situation, highly conductive parts of the tool, like metal areas, might create potential current leakage paths which affect the accuracy and stability of the measurement.

Microwave resonant sensors use spectral feature of a resonator to make high sensitivity measurements of material electromagnetic properties at GHz frequencies. They have been applied to a wide range of industrial and scientific measurements, and used to study a diversity of physical phenomena microwave sensors are used to measure electric permittivity, conductivity, and occasionally magnetic permeability, each of these parameters is a function of the frequency at which the field alternates. A microwave resonant sensor can be designed to measure unambiguously any one of these three parameters at a time. When a material in a resonator interacts with its electromagnetic field, the resonator changes its oscillation frequency and its bandwidth, i.e., the range of frequencies over which it will resonate best. From these parameters, one can deduce the contribution the material has made to the energy storage and energy loss mechanisms within the resonator. Microwave wavelengths are ideally suited to being non-contact detect which permits volumetric measurement to a reasonable depth in a wide range of non-metallic materials. As the microwave sensors are highly flexible in design and do not necessitate specialized materials or fabrication methods, they can be mass-produced at low cost.

It would be advantageous to have a microwave sensor with a simple structure that will penetrate oil-based mud and detect the formation material.

SUMMARY

It is accordingly a general object of the disclosure to measure one or more borehole parameters.

It is a further object of the disclosure to provide a low cost, easy manufactured and highly reliable microwave sensor to determine the formation electrical properties and to image wellbore in oil-based mud.

An embodiment of the disclosure is a wellbore imaging apparatus comprising: at least one microstrip resonator comprising a substrate, a microstrip patch, and a ground plane; at least one slot in the microstrip patch acting as a near-field sensing aperture; and a cable feed to obtain an input impedance match. In an embodiment, the microstrip resonator is used as a sensor. In an embodiment, there is more than one microstrip resonator.

In other embodiments, the wellbore imaging apparatus further comprises a plurality of conducting vias. The microstrip resonator is shorted on all edges by a plurality of conducting vias.

In embodiments of the disclosure, the working frequency of the wellbore imaging tool is from about 0.01 to about 300 GHz. In a preferred embodiment, the working frequency is about 3 GHz.

In further embodiments concerning the microstrip patch, the microstrip patch is circular in shape, and a slot is located at the center of the microstrip resonator. In other embodiments, a plurality of slots are located in the microstrip patch acting as near-field sensing apertures.

In further embodiments concerning the slot, 4 slots are distributed symmetrically along the center of the patch. In certain embodiments, 8 slots are distributed symmetrically along the center of the patch.

In further embodiments concerning the conducting vias, the vias are evenly distributed along the edge of the microstrip patch.

It is a further object of the disclosure to provide a method for wellbore imaging comprising: exciting at least one microstrip resonator by one port in a wellbore; feeding electromagnetic signals to the microstrip resonator by a coaxial cable; detecting the electromagnetic signals to determine resistivity and permittivity of a formation; and generating a borehole image based on the resistivity and/or permittivity of the formation Both of resistivity and permittivity are intrinsic properties of the formation. They depend on the formation structure (e.g. layers, fractures, vugs, etc.) and components (e.g. oil, gas, water etc.). In an embodiment, at least one microstrip resonator is used as a sensor. In an embodiment, there is more than one microstrip resonator excited by one port in a wellbore.

In further embodiments concerning the method for wellbore imaging, detecting resonant frequency, S parameter and quality factor (Q-factor) to determine resistivity and permittivity of a formation; and generating a borehole image based on the apparent resistivity and apparent permittivity. The variation of formation resistivity and permittivity will lead to changes of measured resonant frequency and Q-factor. The method comprises using a microstrip resonator to achieve different S parameters, resonant frequencies and quality factors for different formations. This electromagnetic wave will penetrate the oil-based mud and detect the formation material.

In aspects of the disclosure pertaining to the method for wellbore imaging, a working frequency is from about 0.01 to about 300 GHz. In an embodiment, the working frequency is about 3 GHz.

The foregoing has outlined rather broadly the features of the present disclosure in order that the detailed description that follows can be better understood. Additional features and advantages of the disclosure will be described hereinafter, which form the subject of the claims.

BRIEF DESCRIPTION OF THE DRAWINGS

In order that the manner in which the above-recited and other enhancements and objects of the disclosure are obtained, a more particular description of the disclosure briefly described above will be rendered by reference to specific embodiments thereof which are illustrated in the appended drawings. Understanding that these drawings depict only typical embodiments of the disclosure and are therefore not to be considered limiting of its scope, the disclosure will be described with additional specificity and detail through the use of the accompanying drawings in which.

DETAILED DESCRIPTION

Figure 1:
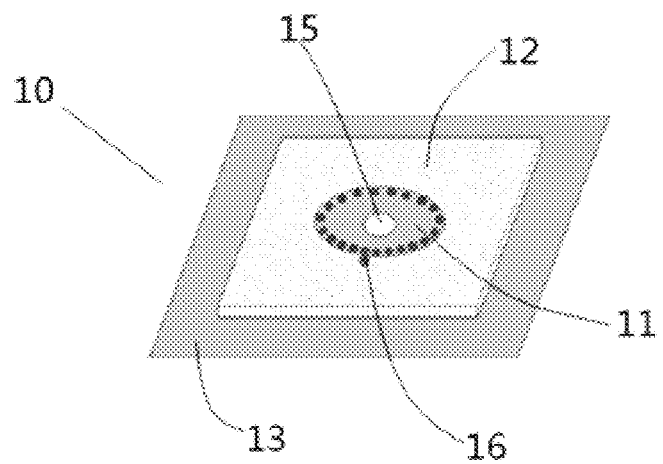
FIG. 1 is a top view of a microstrip resonator in accordance with embodiments disclosed herein.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings making apparent to those skilled in the art how the several forms of the disclosure can be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary $3^{rd}$ Edition.

It is a goal of the present disclosure to measure the formation electrical properties and to image wellbore in oil-based mud. A conventional borehole imager is based on electrical conduction, which does not work when the wellbore is filled with nonconductive oil-based mud.

Still further, it is a goal of the present disclosure to provide an apparatus employing a microstrip resonator as a sensor for electrical measurements of formation as well as wellbore imaging in oil-based mud. An electromagnetic field emitted from a microstrip resonator is used instead of current injected by electrons. This electromagnetic wave penetrates the oil-based mud and detects the formation material.

The property of the formation material monitored by microstrip resonator sensors is permittivity and/or resistivity. Permittivity is a measure of how much electrical energy a material stores and dissipates when it is in an electric field. When an electric field is present, a material will adjust the positioning of its ions or electrons to receive energy from the field. Permittivity is a complex number, the imaginary part of permittivity is the loss factor, a measure of an electric field's energy loss when passing through a material. The real part of permittivity is the dielectric constant, a measure of a material's energy storage when an electric field is present. The shape, size, composition of the formation material can be deduced from the permittivity and/or resistivity parameter. Microstrip resonator sensors allow localization of high field areas. They are very efficient in the frequency band for which they were designed, since the signal-to-noise ratio in a resonator structure increases with resonator quality factor Q. This increase in sensitivity and field strength is accompanied by a narrower frequency band, with the drop amplitude depending on Q, which results from the shift in resonant frequency with different formation material. Consequently, resonance frequency and amplitude tracking are employed. The resonance frequency and amplitude measurements can be converted into pixel intensity values to obtain a borehole wall image.

Regarding the microstrip resonator, in certain embodiments, it includes a reflectometry-type microwave scanning system and uses the near field of the electromagnetic field leaking out of the resonator to achieve different scattering (S) parameters for different formations. The S-parameters describe the electrical behavior of the formation when undergoing various stimuli by electrical signals. The microstrip resonator has high resolution to detect the fractures on the layer. Since near field dissipates very quickly in a lossy formation environment, there is not a multi-path problem like traditional microresistivity tools. The resonator structure has a high Q value, which will help increase the sensitivity in detecting fractures and other features such as bed boundaries, vugs on the borehole wall. The microstrip resonator is conformal and small in size as well as easy to be integrated into a logging tool.

Another embodiment of the disclosure is a method for wellbore imaging in oil-based mud using a cavity-based microstrip resonator with sensing apertures. The method comprises using a microstrip resonator to achieve different S parameters for different formations. This electromagnetic wave will penetrate the oil-based mud and detect the formation material.

Figure 2:
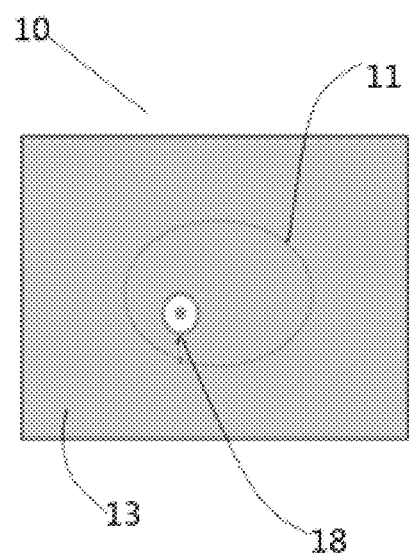
FIG. 2 is a bottom view of a microstrip resonator in FIG. 1.
Figure 3:
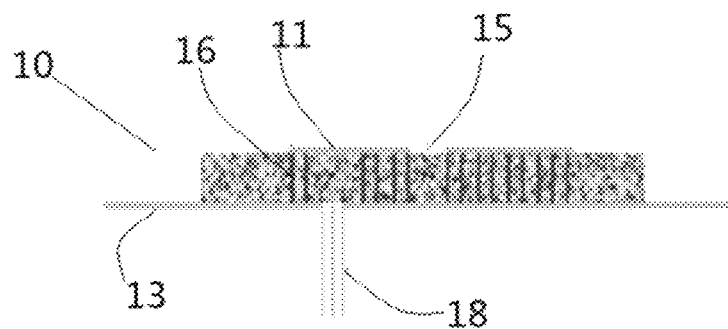
FIG. 3 is a side view of a microstrip resonator in FIG. 1.

The wellbore imaging apparatus disclosed herein contains at least one microstrip resonator. As shown in FIGS. 1-3, the microstrip resonator 10 comprises a patch 11, a substrate 12, and a ground plane 13. The patch 11 is a very thin radiating metal located on one side of a thin no conducting substrate 12. The patch 11 is normally made of thin copper foil plated with a corrosion resistive metal, such as gold, tin, or nickel. The substrate 12 is used primarily to provide proper spacing and mechanical support between the patch 11 and the ground plane 13. It is used with high dielectric-constant material to load the patch and reduce its size. Thickness of the substrate 12 has a big effect on the resonant frequency. In certain embodiments, the thickness of the substrate 12 is 0.01-0.05 of free-space wavelength ($\lambda_0$). The substrate material should be low in insertion loss. In certain embodiments, the substrate material can have a relative dielectric constant in the range of 1.0-2.0. This type of material can be air, polystyrene foam, or dielectric honeycomb. It is further contemplated that other substrate material having a relative dielectric constant in the range of 2.0-4.0 such as fiberglass, reinforced Teflon or having a relative dielectric constant in the range of 4.0-10.0 such as ceramic, quartz and the like can be used. The ground plane 13 is the same metal located on the other side of the substrate 12 and acts a shield to prevent radiation from the antenna being reflected from structures.

Figure 4:
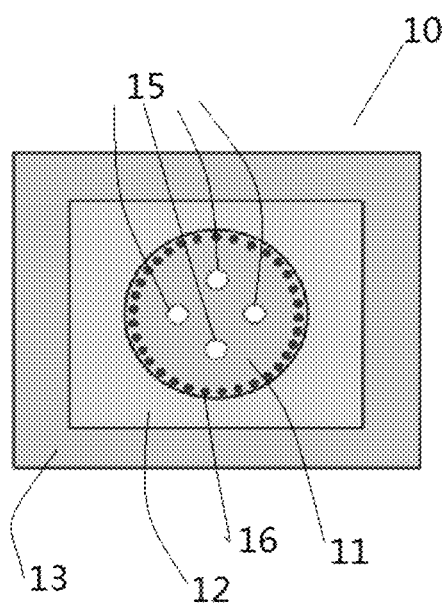
FIG. 4 is a top view of a microstrip resonator with 4 slots in accordance with embodiments disclosed herein.
Figure 5:
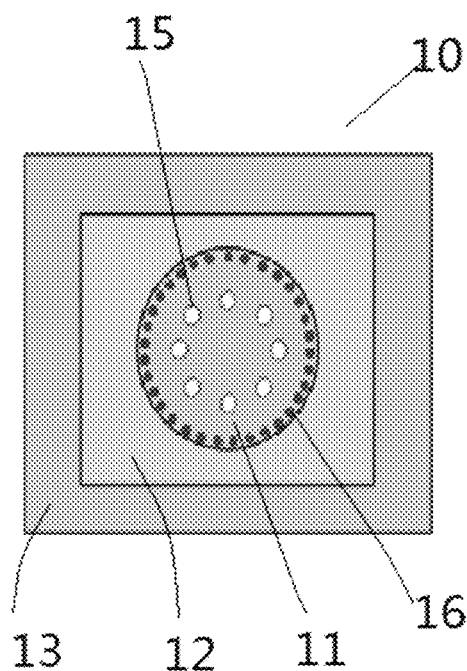
FIG. 5 is a top view of a microstrip resonator with 8 slots in accordance with embodiments disclosed herein.

The patch 11 has a circular shape in certain embodiments. Further, it is contemplated that in some embodiments, the patch can have different shapes such as rectangular, ellipse, triangle, quintuple and the like. A central slot 15 is located in the middle of the patch 11 to act as a near-field sensing aperture. A leaky wave arises from the slot 15 that facilitates energy leakage into the surrounding area, the propagation of the leaky wave depends on the geometry of the microstrip resonator. Although FIG. 1 depicts the slot 15 as circular, the slot 15 can be in different shapes such as rectangular, ellipse, triangle, quintuple and the like to adjust the near field beam. Further, it is contemplated that in some embodiments, there can be multiple slots located in the patch 11, as shown in FIGS. 4 and 5, there are four and eight slots on the top surface, respectively. Different number of slots 15 will lead to different resolution and depth of investigation, thus a Q-factor, or a scattering (S) parameters, or a resonant frequency, or a combination of two or three of them would change. In certain embodiments, referring to FIGS. 4 and 5, 4 or 8 slots 15 are distributed symmetrically along the center of the patch 11, symmetrical distribution of the slots 15 make the direction of the main beam radiating from the slots 15 to be perpendicular to the plane of the patch 11. In other embodiments, unsymmetrical distribution of the slots 15 are also contemplated.

Because of the resonator radiating from one side of the substrate, it is easy to feed it from the other side (the ground plane 13), or from the side of the element. The most important thing to be considered is the maximum transfer of power (matching of the feed line with the input impedance of the antenna), In certain embodiments, referring to FIGS. 1 and 3, the resonator can be fed by a coaxial cable 18 at an appropriate location to obtain a good input impedance match. The inner conductor of the coaxial cable 18 extends through the substrate 12 and is coupled to the patch 11, while the outer conductor of the coaxial cable 18 is connected to the ground plane 13. The input impedance depends on the position of the feed so that the patch can be impedance matched to the line properly positioning the feed. The main advantage of this type of feeding method is that the feed can be placed at any desired location inside the patch in order to match with its input impedance. Further, it is contemplated that in some embodiments, In other embodiments concerning feed, the resonator can be fed by microstrip line, proximity coupling or aperture coupling.

One of the main disadvantages of a microstrip resonator is its strong radiation loss. The open end a microstrip resonator results in a large reflection power of microwave signals the reflection power would cause undesired interference in near field beam arising from the slot 15. To address this issue, reference to FIGS. 1 and 3, the microstrip resonator can optionally include a plurality of electric conducting vias 16 that connects the edge of the patch 11 to the ground plane 13. A vias imposes a deformation in the local field around it, which will depend on its size and position. It will cause a major null of fringe capacitance and the local fields around it. The vias 16 provide an effective mechanism for suppressing the main beam radiating from the slot 15, which will improve radiate effective of the microstrip resonator. The spatial arrangement of the vias 16 can influence the direction of the main beam radiating from the slot 15. In certain embodiments, referring to FIG. 1, a plurality of vias 16 are evenly distributed along the edge of the patch 11, regular spacings between the vias make the direction of the main beam radiating from the slot 15 to be perpendicular to the plane of the patch 11. In other embodiments, irregular spacings between the vias are also contemplated.

Figure 6:
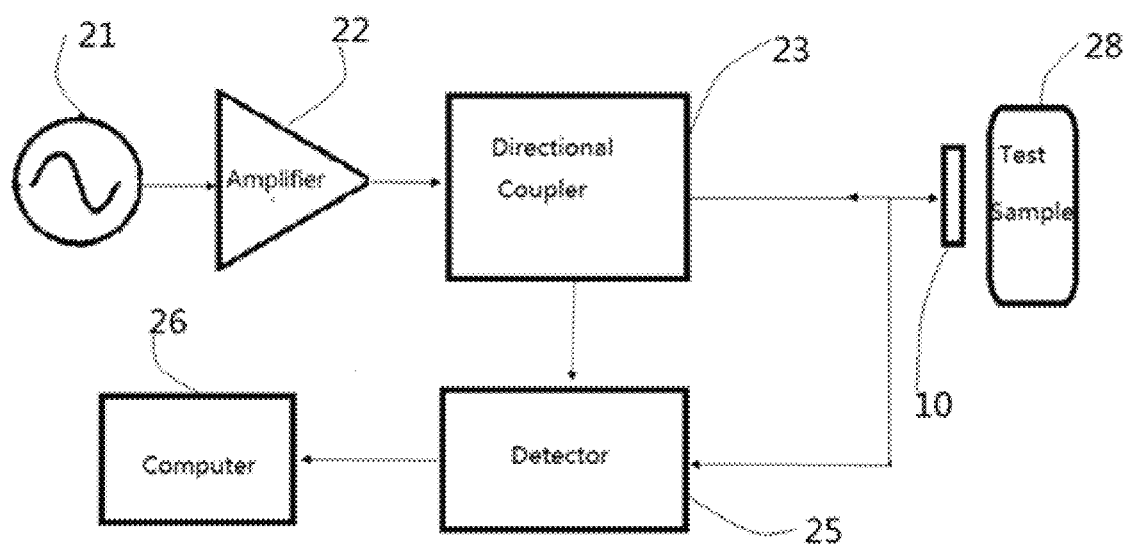
FIG. 6 is a schematic view of a wellbore imaging apparatus in accordance with embodiments disclosed herein.

The schematic for a wellbore imaging apparatus is shown in FIG. 6. A frequency signal generated by an oscillator 21 and amplified by an amplifier 22 is send through a directional coupler 23 and into the test sample 28 by means of a microstrip resonator 10, such that electromagnetic field arises from the slot 15 of microstrip resonator 10 and penetrates the test sample 28. The material of the test sample 28 interacts with the electromagnetic field, and change amplitude and frequency of the electromagnetic field. The same microstrip resonator 10 acts as a receive antenna to detect the signal of reflect wave and transmit the signal to a detector 25. In certain embodiments, the detector 25 includes a phase detect circuit and a magnitude detect circuit. The directional coupler 23 shunts part of the microwave to the detector 25 for phase comparison to the reflected signal. A computer acquisition system 26 samples the detected analogue signals and convert the analogue signals into digital signals by means of an A/D converter. Basic signal processing techniques such as Fast Fourier Transforms and digital filtering are applied to simplify the analysis of the detected signal received from the microstrip resonator 10. The resonance frequency and amplitude measurements can be converted into pixel intensity values to obtain image of the test sample 28. The image can be displayed on a screen connected to the computer.

Because of the high-Q nature of the resonator, the return loss (reflection coefficient) S11 seen by the feeding coaxial cable is very sensitive to the change of formation permittivity and/or resistivity located in proximity of the sensing aperture.

The system is low-profile and small due to the inherent proven advantages of microstrip technology. The system is also very flexible, allowing for a choice of operating frequency, substrate thickness, and aperture size, which can all be adjusted to optimize the sensitivity and penetration ability.

Figure 7:
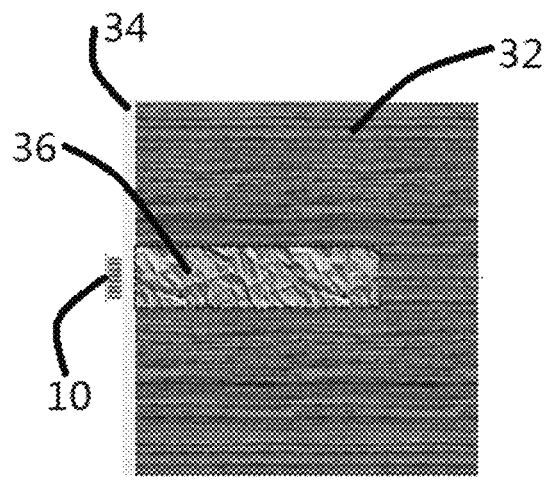
FIG. 7 is a schematic view of an imaging apparatus scanning the fracture of a tested formation.

FIG. 7 shows a schematic of an OBM imaging apparatus scanning over a fracture on an experimental borehole wall. There is a fracture 36 in the formation 32 of the borehole wall, a microstrip resonator 10 is arranged near the fracture 36. The standoff distance between the microstrip resonator 10 and tested formation 32 is 1/8". This means that there will be a thin oil-based mud layer 34 with 1/8" thickness between the microstrip resonator 10 and the tested formation 32. The working frequency can be any frequency that is effective for the apparatus. In certain embodiments, the working frequency is from about 0.01 to about 300 GHz. In this embodiment, the working frequency is set as 3 GHz. The microstrip resonator is excited by one port, which is fed with electromagnetic signals by a coaxial cable. Because different formations correspond to different resistivity and permittivity and the input impedance is resistivity and permittivity dependent. Near field of the electromagnetic field leaking out of the resonator from the aperture will achieve different input impedances, which lead to different scattering (S) parameters, or different resonant frequencies, or different Q-factor, or a combination of two or three of them for different formations. In this embodiment, the formation 32 has permittivity as 40, resistivity as 10 ohm-m, while the fracture 36 is filled with oil-based mud whose permittivity is 4, and resistivity is 10000 ohm-m, the width of the cross fracture is 1/4" and the length is 2".

Figure 8:
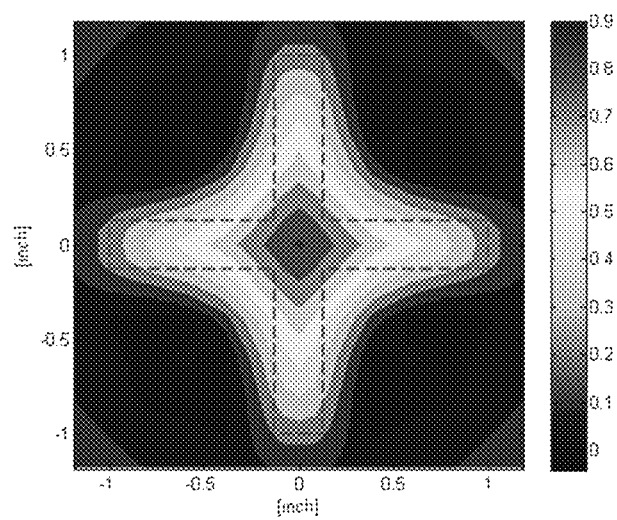
FIG. 8 is a view of a simulated wellbore image.

From the phase detection of signal at the port, the formation resistivity and permittivity can be determined and corresponding borehole images can be generated. FIG. 8 shows a simulated wellbore image, the heavy shadow at the center is the fracture's shape. The imaging apparatus is capable of resolving thin fractures on the borehole wall through oil-based mud.

Figure 9:
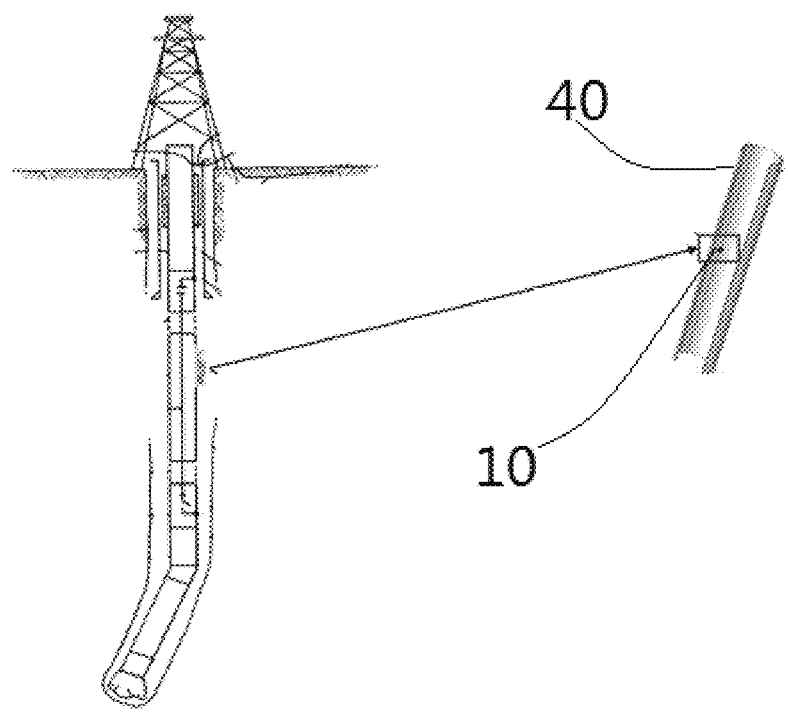
FIG. 9 is a schematic view of an imaging apparatus in a borehole.

FIG. 9 shows a schematic diagram of one embodiment of imaging apparatus in a borehole, a microstrip resonator 10 is deployed against the borehole wall 40 to minimize standoff. Multiple microstrip resonators can be used to obtain measurements over a greater fraction of the borehole's circumference. In some embodiments, the microstrip resonators are provided in axially-offset groups to increase circumferential coverage without undue crowding in the undeployed configuration.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations can be applied to the compositions and methods and in the steps or in the sequence of steps of the methods described herein without departing from the concept, spirit and scope of the disclosure. More specifically, it will be apparent that certain agents which are both chemically related can be substituted for the agents described herein while the same or similar results would be achieved. All such similar substitutes and modifications apparent to those skilled in the art are deemed to be within the spirit, scope and concept of the disclosure as defined by the appended claims.

What is claimed is:

1. A wellbore imaging apparatus comprising:
   at least one microstrip resonator comprising a substrate, a microstrip patch, and a ground plane;
   at least one opening in the microstrip patch acting as a near-field sensing aperture; and
   a cable feed to obtain an input impedance match.

2. The wellbore imaging apparatus of claim 1, wherein there is more than one microstrip resonator.

3. The wellbore imaging apparatus of claim 1, wherein one opening is located at the center of the microstrip resonator.

4. The wellbore imaging apparatus of claim 1, wherein 4 opening are distributed symmetrically along the center of the microstrip patch.

5. The wellbore imaging apparatus of claim 1, wherein 8 opening are distributed symmetrically along the center of the microstrip patch.

6. The wellbore imaging apparatus of claim 1, further comprising a plurality of conducting vias that connect the edge of the patch to the ground plane.

7. The wellbore imaging apparatus of claim 6, wherein the vias are evenly distributed along the edge of the microstrip patch.

8. The wellbore imaging apparatus of claim 1, wherein the microstrip patch is circular in shape.

9. The wellbore imaging apparatus of claim 1, wherein a working frequency is from about 0.01 to about 300 GHz.

10. The wellbore imaging apparatus of claim 8, wherein the working frequency is about 3 GHz.

11. A method for wellbore imaging comprising:
    exciting at least one microstrip resonator by one port in a wellbore;
    feeding electromagnetic signals to the microstrip resonator by a coaxial cable;
    detecting electromagnetic signals to determine resistivity and/or permittivity of a formation; and
    generating a borehole image based on the resistivity and/or permittivity of the formation.

12. The method of claim 11, wherein the electromagnetic signals are phase or amplitude of resonant frequency.

13. The method of claim 11, wherein there is more than one microstrip resonator excited by one port in a wellbore.

14. The method of claim 11, wherein a working frequency is from about 0.01 to about 300 GHz.

15. The method of claim 14, wherein the working frequency is about 3 GHz.

* * * * *